(12) United States Patent
Batts et al.

(10) Patent No.: US 6,544,991 B2
(45) Date of Patent: Apr. 8, 2003

(54) COMPOSITIONS AND METHODS FOR TREATING BACTERIAL INFECTIONS

(75) Inventors: Donald H. Batts, Kalamazoo, MI (US); Keiichi Hiramatsu, Tokyo (JP)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/886,641

(22) Filed: Jun. 21, 2001

(65) Prior Publication Data

US 2002/0022610 A1 Feb. 21, 2002

Related U.S. Application Data

(60) Provisional application No. 60/279,306, filed on Mar. 28, 2001, provisional application No. 60/232,773, filed on Sep. 15, 2000, and provisional application No. 60/215,418, filed on Jun. 30, 2000.

(51) Int. Cl.[7] ............................................. A61K 31/535
(52) U.S. Cl. ................ 514/235.5; 514/236.8; 514/376; 514/192; 514/198
(58) Field of Search .................. 514/376, 235.5, 514/236.8, 198, 192

(56) References Cited

U.S. PATENT DOCUMENTS

| | | | |
|---|---|---|---|
| 2,985,648 A | 5/1961 | Doyle et al. ............. 260/239.1 |
| 3,144,445 A | 8/1964 | Grant et al. ............. 260/239.1 |
| 4,234,579 A | 11/1980 | Barth ...................... 424/426 |
| 5,529,998 A | 6/1996 | Häbich et al. ............ 514/233.8 |
| 5,547,950 A | 8/1996 | Hutchinson et al. ........ 514/252 |
| 5,627,181 A | 5/1997 | Riedl et al. ................ 514/236 |
| 5,684,024 A | 11/1997 | Riedl et al. ................ 514/337 |
| 5,688,792 A | 11/1997 | Barbachyn et al. ....... 514/235.5 |
| 5,698,574 A | 12/1997 | Riedl et al. ................ 514/376 |
| 5,700,799 A | 12/1997 | Hutchinson et al. ..... 514/235.8 |
| 5,792,765 A | 8/1998 | Riedl et al. ................ 514/236.8 |
| 5,827,857 A | 10/1998 | Riedl et al. ................ 514/301 |
| 5,837,870 A | 11/1998 | Pearlman et al. ........... 544/137 |
| 5,843,967 A | 12/1998 | Riedl et al. ................ 514/340 |
| 5,861,413 A | 1/1999 | Habich et al. ............. 514/312 |
| 5,869,659 A | 2/1999 | Stolle et al. ............... 514/114 |
| 5,880,118 A | 3/1999 | Barbachyn et al. ......... 514/211 |
| 5,968,962 A | 10/1999 | Thomas et al. ............. 514/376 |
| 5,981,528 A | 11/1999 | Gravestock ................ 514/252 |

FOREIGN PATENT DOCUMENTS

| | | |
|---|---|---|
| GB | 902703 | 8/1962 |
| WO | WO 99/24393 | 5/1999 |
| WO | WO 00/44741 | 8/2000 |

OTHER PUBLICATIONS

Kato et al., "*In Vitro* Synergy between Linezolid and Sulbactum/Ampicillin against Methicillin–Resistant *Staphylococcus aureus* Clinical Isolates Including those with Reduced Susceptibility to Vancomycin," Abstracts of the Interscience Conference on Antimicrobial Agents & Chemotherapy, 40:184 (2000).

International Search Report in PCT/US01/19712 dated Jul. 23, 2002.

Campoli–Richards et al., "Sulbactum/ampicillin. A Review of its Antibacterial Activity, Pharmacokinetic Properties, and Therapeutic Use," *Drugs*, 33:577–609 (1987).

Methar et al., "A Non–comparative Study of Parenteral Ampicillin and Sulbactam in Intra–thoracic and Intra–abdominal Infections," *J. Antimicrob. Chemother.*, 17:389–396 (1986).

Sweeney et al., "In vitro activity of Linezolid Combined with other Antibacterial Agents," Poster Presentation No. 1252. No Date Given.

International Preliminary Examination Report for PCT/US01/19712 dated Oct. 17, 2002.

*Primary Examiner*—Dwayne C. Jones
*Assistant Examiner*—C. Delacroix-Muirheid
(74) *Attorney, Agent, or Firm*—James D. Darnley; Pharmacia & Upjohn Company

(57) ABSTRACT

A composition having antibacterial activity is disclosed. More particularly, a mixture of an oxazolidinone compound, sulbactam, and ampicillin active agents, demonstrating activity against resistant strains of bacteria is disclosed. Methods for using an oxazolidinone compound, sulbactam, and ampicillin to treat a bacterial infection are also described.

30 Claims, No Drawings

COMPOSITIONS AND METHODS FOR TREATING BACTERIAL INFECTIONS

This application claims priority to U.S. patent application Ser. No. 60/215,418, filed Jun. 30, 2000, U.S. patent application Ser. No. 60/232,773, filed Sep. 15, 2000, and 60/279,306, filed Mar. 28, 2001, the respective disclosures of which are each incorporated herein by reference.

BACKGROUND OF THE INVENTION

1. Field of the Invention

The invention relates to compositions having antibacterial activity, and methods of treating bacterial infections. More particularly, the invention relates to the use of an oxazolidinone compound, sulbactam, and ampicillin in treating a patient having a bacterial infection.

2. Description of the Related Technology

Many classes of compounds, including aminoglycosides, oxazolidinones, and β-lactams, have been described for the treatment of infectious diseases, particularly bacterial infections. As the use of the these antibacterial agents becomes more widespread, the emergence of new resistant strains of bacteria is imminent. The new resistant strains, for example, methicillin-resistant *Staphylococcus aureus* (MRSA), vancomycin-resistant Enterococci (VRE), vancomycin-resistant *Staphylococcus aureus* (VRSA), glycopeptide-intermediate *Staphylococcus aureus* (GISA), and vancomycin-intermediate *Staphylococcus aureus* (VISA), have reduced susceptibility to known antibacterial agents, creating an ongoing need for developing effective therapeutic measures.

Oxazolidinones are known to have good activity against gram-positive microorganisms. In particular, the oxazolidinone compounds have demonstrated beneficial characteristics in treating urinary tract infections, caused by resistant bacterial agents including infections induced by vancomycin-resistant Enterococci.

The β-lactam, D-(−)-α-aminobenzylpenicillin (ampicillin), has been described as a useful nutritional supplement for the treatment of mastitis in cattle, and as an antibacterial therapeutic agent in poultry and human beings. Another β-lactam compound, penicillanic acid, 1,1-dioxide (sulbactam), has been described for enhancing the effectiveness of several β-lactam antibiotics, including ampicillin. The synergistic antibacterial activity of an ampicillin active agent in combination with sulbactam is reported in *Drugs* 33, 577–609 (1987) and *J. Antimicrob. Chemother.* 17, 389–396 (1986).

Despite the known activities of oxazolidinone and β-lactam compounds, there remains an ongoing need for additional antibacterial compositions. A beneficial composition would provide a method for treating bacterial infections caused by resistant strains of infectious agents.

SUMMARY OF THE INVENTION

In one aspect, the invention relates to a composition containing an oxazolidinone compound, sulbactam, and ampicillin active agents. The composition demonstrates antibacterial activity against a broad spectrum of antibacterial agents.

In another aspect, the invention relates to method of treating a bacterial infection comprising administering oxazolidinone, sulbactam, and ampicillin active agents. The method encompasses the administration of antibacterial effective amounts of oxazolidinone and ampicillin and an antibacterial enhancing amount of sulbactam, separately or in admixture.

Yet another aspect of the invention relates to the use of a composition comprising an antibacterial effective amount of an oxazolidinone, an antibacterial effective amount of ampicillin, and an antibacterial enhancing amount of sulbactam for the manufacture of a medicament for preventing or treating a bacterial infection.

These and other aspects, advantages, and features of the invention will become apparent from the following detailed description of the invention.

DETAILED DESCRIPTION OF THE INVENTION

The invention relates to the administration of effective amounts of active agents useful for treating bacterial infections and, more particularly, bacterial infections caused by extremely resistant bacterial microorganisms. The treatment of the invention exhibits antibacterial activity against isolates of various extremely resistant strains of bacteria including, for example, but not limited to, staphylococci, enterococci, and steptococci that are sensitive or resistant to various antibiotics such as penicillins, cephalosporins, aminoglycosides, glycopeptides, macrolides, quinolones, steptogramins, and lipopeptides.

The enhanced activity of an oxazolidinone, for example linezolid, when used in combination with sulbactam and ampicillin provides a surprisingly effective, synergistic activity in treating resistant strains of bacteria, including extremely resistant strains of bacteria such as MRSA, VRE, VRSA, GISA, and VISA.

As used herein, the term "antibacterial effective amount" refers to an amount effective to prevent development of, or to alleviate any existing symptoms of an infection caused by bacteria, for example, particularly resistant strains of staphylococci, enterococci, and streptococci.

The term "antibacterial enhancing amount", as used herein, refers to an amount sufficient to provide a synergistic, typically more than additive, effect when used in combination with a desired antibacterial agent. Determination of an "antibacterial effective amount" and "antibacterial enhancing amount" is well within the capability of those skilled in the art, especially in light of the detailed disclosure provided herein.

In previously unreported efforts, scientists at Pharmacia Corporation (Kalamazoo, Mich., U.S.A.) have observed imperceptible differences between the antibacterial activity of linezolid alone and the activity of linezolid in combination with ampicillin. See, In vitro *Activity of Linezolid Combined with other Antibacterial Agents,* Poster Presentation, No. 1252. In light of the absence of synergistic activity between linezolid and ampicillin, it is a surprising result that linezolid demonstrates synergistic activity with a combination of sulbactam and ampicillin.

Oxazolidinones suitable for the invention typically are gram-positive antibacterial agents. Certain oxazolidinone compounds useful in the invention have been described in U.S. Pat. No. 5,688,792 and in U.S. Pat. No. 5,880,118, the entire disclosures of which are both incorporated herein by reference. Suitable oxazolidinone compounds have the formula:

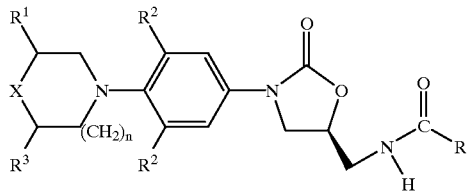

or is a pharmaceutically acceptable salt thereof, wherein:
X is O, S, SO, $SO_2$, $SNR^{11}$, $NC(O)R^{11}$, and $S(O)NR^{11}$;
n is 0, 1, or 2;
R is selected from the group consisting of:
hydrogen;
$C_1$–$C_8$ alkyl optionally substituted with one or more substituents selected from the group consisting of F, Cl, hydroxy, $C_1$–$C_8$ alkoxy, $C_1$–$C_8$ acyloxy, or —$CH_2$— phenyl;
$C_3$–$C_6$ cycloalkyl;
amino;
$C_1$–$C_8$ alkylamino;
$C_1$–$C_8$ dialkylamino; or
$C_1$–$C_8$ alkoxy;
$R^1$ at each occurrence is hydrogen, except when X is O, then $R^1$ is independently selected from the group consisting of H, $CH_3$, CN, $CO_2H$, $CO_2R$, and $(CH_2)_mR^{10}$, wherein m is 1 or 2;
$R^2$ at each occurrence is independently selected from the group consisting of H, F, and Cl;
$R^3$ is H, except when X is O and $R^1$ is $CH_3$, then $R^3$ is H or $CH_3$;
$R^{10}$ is selected from the group consisting of H, OH, OR, OCOR, $NH_2$, NHCOR, and $N(R^{11})_2$; and
$R^{11}$ at each occurrence is independently selected from the group consisting of H, p-toluensulfonyl, and $C_1$–$C_4$ alkyl optionally substituted with one or more substituents selected from the group consisting of Cl, F, OH, $C_1$–$C_8$ alkoxy, amino, $C_1$–$C_8$ alkylamino, and $C_1$–$C_8$ dialkylamino.

The carbon content of various hydrocarbon-containing moieties is indicated by a prefix designating the minimum and maximum number of carbon atoms in the moiety, i.e., the prefix $C_i$–$C_j$ defines the number of carbon atoms present from the integer "i" to the integer "j" inclusive. Thus, $C_1$–$C_4$ alkyl refers to an alkyl group of 1 to 4 carbon atoms, inclusive, for example, methyl, ethyl, propyl, isopropyl, butyl, and tert-butyl. $C_1$–$C_8$ alkyl is methyl, ethyl, propyl, butyl, pentyl, hexyl, heptyl, octyl, and isomeric forms thereof.

As used herein, the term "pharmaceutically acceptable salts" refers to organic and inorganic acid addition salts of the parent compound. Examples of salts useful for the invention are, for example, hydrochloride, hydrobromide, hydroiodide, sulfate, phosphate, acetate, propionate, lactate, mesylate, maleate, malate, succinate, tartrate, citrate, 2-hydroxyethyl sulfate, fumarate, and the like.

One suitable oxazolidinone compound having the structure,

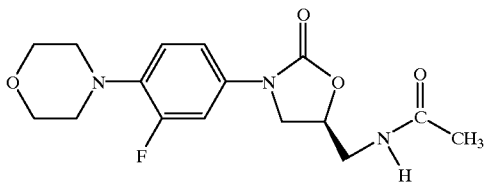

has the IUPAC name (S)-N-[[3-[3-fluoro-4-(4-morpholinyl) phenyl]-2-oxo-5-oxazolidinyl]methyl]acetamide. The compound is commonly known as linezolid and has demonstrated particularly effective antibacterial activity.

The linezolid compound can be prepared according any suitable method, including for example, general methods described in U.S. Pat. No. 5,688,792. Briefly, the heteroaryl substituent, for example an oxazine or thiazine moiety, is reacted with a functionalized nitrobenzene in the presence of a suitable base, preferably in an organic solvent, such as acetonitrile, tetrahydrofuran, or ethyl acetate. The nitro group is reduced either by hydrogenation or using a suitable reducing agent, for example aqueous sodium hydrosulfite, to afford an anilo compound. The anilo compound is converted into its benzyl or methyl urethane derivative, deprotonated with a lithium reagent to give a suitable lithiated intermediate, and treated with (−)-(R)-glycidyl butyrate to afford a crude oxazolidinone compound. A suitable method for preparing the linezolid compound is more particularly described in Example 5 of U.S. Pat. No. 5,688,792.

Another oxazolidinone compound having the structure,

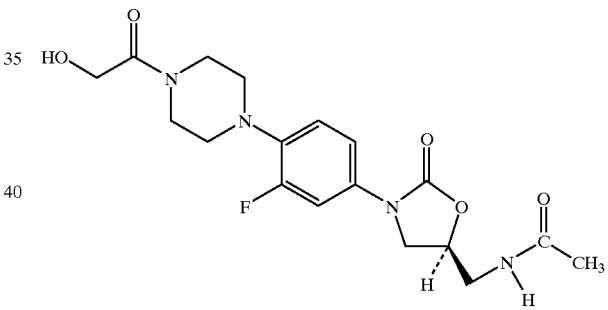

has the IUPAC name (S)-N-[[3-[3-fluoro-4-[4-(hydroxyacetyl)-1-piperazinyl]-phenyl]-2-oxo-5-oxazolidinyl]methyl]acetamide. More commonly known as eperezolid, the compound is a preferred compound which can be incorporated into the composition of the invention. The eperezolid compound can be prepared by any suitable method.

An advantageous process for preparing oxazolidinones, including eperezolid, is described in U.S. Pat. No. 5,837,870, the entire disclosure of which is incorporated herein by reference. Generally, the process involves providing a 5-hydroxymethyl substituted oxazolidinone alcohol from a carbamate or trifluoroacetamide using a dihydroxy compound or glycidol starting material. The hydroxymethyl substituted oxazolidinone alcohol is transformed to the corresponding amino compound, such as 5-aminomethyl substituted oxazolidinone amines, which are acylated to form useful antibacterial 5-acylamidomethyl substituted oxazolidinone compounds. A suitable method of preparing the eperezolid compound is more particularly described in Example 8 of U.S. Pat. No. 5,837,870.

Yet another compound suitable for use in the invention is a compound of the structure:

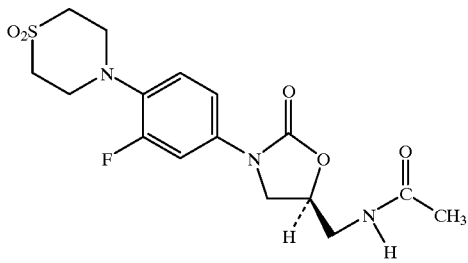

having the IUPAC name, (S)-N-[[3-[3-fluoro-4-(tetrahydro-2H-thiopyran-4-yl)phenyl]-2-oxo-5-oxazolidinyl]methyl] acetamide S,S-dioxide. A method for preparing the compound is more particularly described in Example 51 of U.S. Pat. No. 5,968,962, the entire disclosure of which is incorporated herein by reference.

Another compound suitable for the invention has the structure:

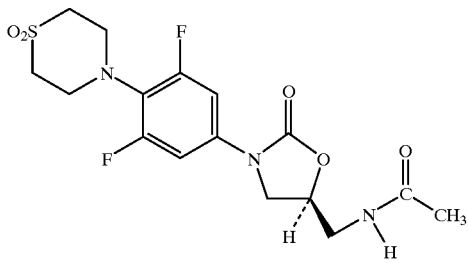

having the IUPAC name (S)-N-[[3-[3,5-difluoro-4-(tetrahydro-2H-thiopyran-4-yl)phenyl]-2-oxo-5-oxazolidinyl]methyl]acetamide S,S dioxide. The compound and a method for preparing the compound are described in U.S. Pat. No. 5,880,118, the entire disclosure of which is incorporated herein by reference.

According to the invention, an oxazolidinone compound having similar structure or physiochemical properties as any oxazolidinone group described above will be expected to demonstrate synergistic activity with sulbactam and ampicillin. To identify such oxazolidinone compounds, the compound to be tested can substitute linezolid, eperezolid, or any compound of the general oxazolidinone structure in the method of the invention and analyzed for antibacterial activity by any suitable method.

Linezolid and eperezolid can be prepared by the processes set forth in U.S. Pat. Nos. 5,688,792 and 5,837,870 as well as that of International Publication No. WO 99/24393, published May 20, 1999, the respective disclosures of which are incorporated herein by reference. In addition, (S)-N-[[3-[3-fluoro-4-(tetrahydro-2H-thiopyran-4-yl)phenyl]-2-oxo-5-oxazolidinyl]methyl]acetamide S,S-dioxide can be prepared according to the methods described in U.S. Pat. No. 5,968,962, or the process of International Publication No. WO 00/44741, published Aug. 3, 2000, the entire disclosure of which is incorporated herein by reference. The general methods described in U.S. Pat. No. 5,880,118, which is incorporated herein by reference, also are useful for preparing (S)-N-[[3-[3,5-difluoro-4-(tetrahydro-2H-thiopyran-4-yl)phenyl]-2-oxo-5-oxazolidinyl]methyl]acetamide S,S dioxide.

Linezolid can exist in at least two crystal forms. It is preferred that the linezolid incorporated in the composition of the invention has a crystal Form II. Crystal Form II of linezolid has the powder X-ray diffraction pattern as follows in the table below:

| d-Spacing (Å) | Two-Theta Angle (°) | Relative Intensity (%) |
| --- | --- | --- |
| 12.44 | 7.10 | 2 |
| 9.26 | 9.54 | 9 |
| 6.37 | 13.88 | 6 |
| 6.22 | 14.23 | 24 |
| 5.48 | 16.18 | 3 |
| 5.28 | 16.79 | 100 |
| 5.01 | 17.69 | 2 |
| 4.57 | 19.41 | 4 |
| 4.50 | 19.69 | 2 |
| 4.45 | 19.93 | 6 |
| 4.11 | 21.61 | 15 |
| 3.97 | 22.39 | 23 |
| 3.89 | 22.84 | 4 |
| 3.78 | 23.52 | 7 |
| 3.68 | 24.16 | 1 |
| 3.52 | 25.28 | 13 |
| 3.34 | 26.66 | 1 |
| 3.30 | 27.01 | 3 |
| 3.21 | 27.77 | 1 |

The infrared (IR) spectrum (mineral oil mull) of the Form II crystal follows: 3364, 1748, 1675, 1537, 1517, 1445, 1410, 1401, 1358, 1329, 1287, 1274, 1253, 1237, 1221, 1145, 1130, 1123, 1116, 1078, 1066, 1049, 907, 852 and 758 $cm^{-1}$.

Crystal Form II is prepared from a linezolid compound of high enantiomeric purity, preferably at least 98% enantiomerically pure. It is more preferred that the linezolid be more than 99% pure and it is even more preferred that the linezolid be at least 99.5% pure.

Crystal Form II of linezolid can be prepared either from a solution of linezolid or from the solid. The linezolid starting material, solid or solution, is mixed with a suitable solvent. Examples of suitable solvents are water; acetonitrile; chloroform; methylene chloride; a solvent of the formula $R^{21}$—OH, wherein $R^{21}$ is $C_1$–$C_6$ alkyl; a solvent of the formula $R^{21}$—CO—$R^{22}$ wherein $R^{22}$ is $C_1$–$C_6$ alkyl and $R^{21}$ is as defined above; and phenyl substituted with one, two, or three $R^{21}$ groups, wherein $R^{21}$ is as defined above; and a solvent of the formula $R^{21}$—CO—O—$R^{22}$, wherein $R^{21}$ is $C_1$–$C_6$ alkyl and $R^{22}$ is as defined above. It is preferred that the solvent is ethyl acetate, methanol, ethanol, propanol, isopropanol, butanol, acetonitrile, acetone, methyl ethyl ketone, chloroform, methylene chloride, toluene, xylene, diethyl ether, or methyl-t-butyl ether. It is more preferred that the solvent is ethyl acetate, acetone, acetonitrile, propanol, or isopropanol. The most preferred solvent is ethyl acetate.

The mixture of linezolid in the solvent is agitated at a temperature below 80° C. until linezolid Form II crystals are formed and crystals of other solid forms, such as Form I, disappear. It is preferred to dissolve the linezolid in ethyl acetate at a temperature near the boiling point of the solvent. The mixture is cooled to a temperature of about 70° C. The mixture may be seeded with crystals of Form II to facilitate crystallization. In a preferred method of preparing the Form II crystal, the solid product is cooled and agitated at a temperature between about 45° C. and about 60° C. until the solids consist only of Form II crystals. It is most preferred to maintain the slurry at a temperature of about 55° C. Preferably, the linezolid and solvent are mixed for at least 10 minutes to obtain a desired mixture. More preferably, the linezolid and solvent are mixed for at least 20 minutes, or even more preferably for at least 30 minutes. The time and temperature will vary depending on the solvent selected. With ethyl acetate it is preferred to mix for not less than 60 minutes. The crystalline slurry may be further cooled to improve yield, and the solid Form II product may be isolated. Other measures which can be used to facilitate crystallization include, but are not limited to, cooling, concentrating the solution by evaporation or distillation, or adding other solvents. The formed crystals can be isolated by any method. Various methods for isolating crystals are readily available to one with skill in the art.

The ampicillin (i.e., α-aminobenzylpenicillin) compound

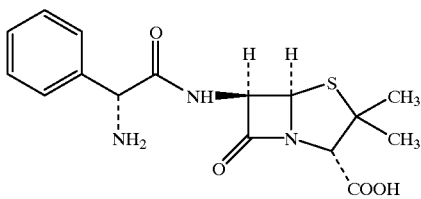

is suitable for use in the invention, and previously has been described as an antibacterial agent. More particularly, the ampicillin compound has been described in at least U.S. Pat. Nos. 2,985,648 and 3,144,445; and British Patent Specification No. 902,703, the respective disclosures of which are incorporated herein by reference. The compounds can be prepared by any suitable method, including at least the reaction of 6-aminopenicillanic acid, preferably as a neutral salt, with an acid chloride derivative of the acylated benzyl group. The primary amino group is removed thereafter and hydrogenated under mild conditions to provide the ampicillin compound.

Sulbactam, or penicillanic acid 1,1-dioxide, having the structure

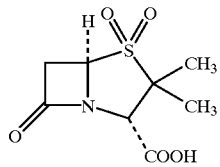

has been described as an agent for enhancing the effectiveness of β-lactam antibiotic agents, including for example ampicillin. The use of penicillanic acid 1,1-dioxide compounds for enhancing antibacterial activity is described in U.S. Pat. No. 4,234,579, the disclosure of which is herein incorporated by reference.

The methods and compositions of the invention are particularly effective against resistant strains of bacterial infection including, for example, resistant strains of *Staph. aureus*. More particularly, the methods and compositions of the invention can be useful in treating diseases caused by MRSA, VRSA, or VISA. Examples of conditions which can treated by a composition of the invention include, but are not limited to, endocarditis, osteomyelitis, meningitis, skin and skin structure infections, pneumonias, bacteremias, intra-abdominal infections, genitourinary tract infections, abscesses, necrotizing infections, and the like. The conditions more particularly can include diabetic foot infections, decubitus ulcers, burn infections, animal or human bite wound infections, synergistic-necrotizing gangrene, necrotizing fasciitis, intra-abdominal infection associated with breeching of the intestinal barrier, pelvic infection associated with breeching of the intestinal barrier, aspiration pneumonia, and post-operative wound infections.

One advantage of the synergistic activity demonstrated by the invention is that relatively small amounts of the active agents can be used to obtain a high level of antibacterial activity. Typically, special care is taken to avoid introducing unnecessary drugs or active substances in patients having neutropenia, i.e. a condition characterized by a decrease in white blood cells, chiefly in the neutrophils. The invention allows high levels of antibacterial effect to be achieved using relatively small amounts of active agent than when compared with the individual antibacterial components used in the invention. This advantage can be particularly beneficial in patients having neutropenia, such as patients suffering from leukemia or lymphoma.

In addition, the combined use of the oxazolidinone compound, particularly linezolid, with sulbactam and ampicillin provides a new broad spectrum of antibacterial activity. The methods and compositions demonstrate antibacterial activity against a broad spectrum of gram-positive and gram-negative infectious agents, including gram-negative aerobes and anaerobes. Moreover, the invention allows more rapid and complete elimination of difficult to treat gram-positive infections, particularly in difficult to penetrate regions of the body where local conditions are unfavorable toward eliminating the microorganism by a single antibacterial agent.

The composition can be administered in accordance with the method of the invention. The method provides for treating an antibacterial infection comprising administering, singly or together, oxazolidinone, sulbactam, and ampicillin active agents. The active agents may, but need not, be admixed to provide a mixture having therapeutic activity. Alternatively, the active agents may be administered separately, or two of the three active agents may be combined and administered separately of the third active agent.

The active agents may be incorporated into pharmaceutically acceptable carriers to facilitate the administration of the active agents. As used herein, the term "pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Any conventional pharmaceutical preparation can be used. The pharmaceutical composition generally will comprise an inert pharmaceutical carrier and an effective dose of the active substance. Examples of dosage forms suitable for the invention are plain or coated tablets, capsules, lozenges, powders, solutions, suspensions, emulsions, syrups, and other useful mediums for delivering the active agent. Generally, the composition of the invention can be administered orally or intraveneously. The preferred pharmaceutically acceptable carrier is an oral dosage form comprising one or more inert excipients, for example, mannitol, maize starch, colloidal silica, povidone, and magnesium stearate.

An aqueous solution for intravenous ("IV") administration can be placed in a suitable container such as a bag, a bottle, a vial, a large volume parenteral, a small volume parenteral, a prefilled syringe or a cassette. As used herein, the term "bottle" to refers to larger bottles, typically having a fill volume, i.e. the amount of liquid contained in an unused product, of at least 20 mL. The term "vials" as used herein refer to smaller bottle-shaped containers, typically having a fill volume of less than 20 mL, for example in units of 1 mL, 2 mL, 5 mL, and the like. It is preferred that the container is bag, a bottle, a vial or a prefilled syringe. The more preferred container is a bag or bottle. The most preferred container is a bag. When so used, it is preferred that the bag has sufficient capability to hold 25 mL to 2,000 mL of IV solution. For a bag, amounts of 100 mL, 200 mL, or 300 mL portions of solution are preferred for each bag. However, larger and/or smaller volumes also are acceptable.

The intravenously administered solution is introduced into the patient as a sterile liquid. While there are a number of methods to sterilize an IV solution, it is preferred that the IV solution is sterilized by terminally moist heat or steam sterilization. When the term terminally "moist heat sterilize" is used, it refers to and includes steam sterilization.

To sterilize the solution using terminally moist heat sterilization, the solution is placed in the container suitable for transporting the solution and as a receptacle for holding the solution during administration of the solution. Accordingly, the container is chosen in such a manner as to avoid reacting with the pharmaceutically active ingredient, for example an oxazolidinone compound, during sterilization, transport, or administration.

A container comprising at least 50% polyolefin provides a significant advantage in the storage of linezolid solutions, in particular. One desirable benefit of polyolefin-type containers is that the loss of linezolid during and following terminal moist heat sterilization is minimized. It is particularly beneficial when the primary container-solution contact surface material is the polyolefin. The remainder of the container can be made from polyolefin or other materials. It is preferred that the container-solution contact surface is made from about 50% to about 100% polyolefin. A more preferred container-solution contact surface has from about 70% to about 90% polyolefin. An even more preferred container-solution contact surface comprises from about 75% to about 85% polyolefin.

Polyolefins include, for example, polyethylenes, polypropylenes, polybutenes, polyisoprenes, and polypentenes and copolymers and mixtures thereof. It is preferred that the polyolefin is polyethylene or polypropylene. A preferred polyolefin is polypropylene or mixture of polypropylene and polyethylene.

The methods and compositions of the invention can be used to treat humans and mammals such as, for example, horses, cattle, dogs, cats, sheep, and pigs.

The treatment regimen of the compositions, for example the dosage and frequency of administration, depends on a variety of factors, including, for example, the oxazolidinone compound used, the infection being treated, the severity of the condition being treated, the age, weight, general physical condition of the particular patient, other medication the individual may be taking as is well known to those skilled in the art and can be more accurately determined by measuring the blood level or concentration of the antibacterial oxazolidinone in the patient's blood and/or the patient's response to the particular condition being treated.

Typically, the antibacterial oxazolidinone can be administered two or three times daily, depending on the place of the infection, the severity of the disease, the size and the age of the patient. In pediatric patients, the adult dose is appropriately reduced for the child based on the size of the child. Oxazolidinones clear very rapidly from the body in young children, particularly those children having less than or about five years of age. Accordingly, a patient of about five years of age or less may require an appropriately adjusted dose three times a day administration. Also, patients who do not respond well to twice daily dosing may require three times a day administration. In general, twice daily administration is preferred.

The amounts of the active agents to be administered can be readily determined by any method available to one with skill in the art of providing therapeutic treatments. To guide the reader in the practice of the invention, generally an amount of from about 200 mg to about 900 mg of the oxazolidinone is administered to the patient, typically either twice a day (b.i.d.) or three times a day (t.i.d.). Preferably, the amount of the oxazolidinone is about 500 mg to about 700 mg every 12 hours. The total drug concentration of the ampicillin/sulbactam component of the invention is from about 3.1 gm to about 6.2 gm, preferably administered every four to eight hours. A course of treatment for an adult patient can last from about seven days to about 60 days.

The response of the patient to the treatment can be followed by standard clinical, radiological, microbiological, and other laboratory investigations. In particular, serum cidal assays can be carried out to generate an inhibitor or cidal titer to aid in determining the specific dose to the patient. Typically, the treatment will last from about 14 days to about 28 days. For young children, especially those about age five and under, the preferred dose is about 10 mg/kg twice daily.

In another aspect, the amounts of active agents can be incorporated into a composition for the manufacture of a medicament suitable for therapeutic use. At least two of the active agents, an oxazolidinone, ampicillin, and sulbactam, can be incorporated into a pharmaceutically acceptable carrier for preventing or treating infection as previously described.

Without further elaboration, it is believed that one skilled in the art can, using the preceding description, practice the invention to its fullest extent. The following detailed examples describe how to prepare the various compounds and/or perform the various processes of the invention and are to be construed as merely illustrative, and not limitations of the preceding disclosure in any way whatsoever. Those skilled in the art may recognize appropriate variations from the procedures both as to reactants and as to reaction conditions and techniques.

EXAMPLES

Synergistic Activity of Linezolid with Sulbactam and Ampicillin

Bacterial isolates were obtained from human infections. The isolates were maintained frozen in a liquid nitrogen freezer and plated on Trypticase Soy Agar (TSA) plates supplemented with 5% sheep blood. The quality control strain *Staph. aureus* 29213 was originally acquired from the American Type Culture Collection (Rockville, Md.).

The antibiotic powders used were obtained from the following sources: linezolid (LZD) was obtained from Pharmacia Corporation (Kalamazoo, Mich., U.S.A.); ampicillin (ABPC) and sulbactam (SBT), or ampicillin/sulbactam (S/A), were obtained from Pfizer Inc. (New York, N.Y., U.S.A.); teicoplanin (TEIC) was obtained from Aventis Pharma Ltd. (Parsippany, N.J., U.S.A.); vancomycin (VCM) and oxacillin (MPIPC) were obtained from Sigma Chemical Company, St. Louis, Mo., U.S.A.); arbekacin (ABK) was obtained from Meiji Seika Co. (Tokyo, Japan); ceftizoxime (CZX) was obtained from Fujisawa Pharmacy Co. (Osaka, Japan); and imipenem (IMP) was obtained from Banyu Co. (Tokyo, Japan).

MICs were determined by an agar dilution method or microbroth dilution method recommended by NCCLS. Synergy was assessed by agar dilution checker-board method. Minimal inhibitory concentrations (MICS) for each separate drug were determined. The fractional inhibitory concentration (FIC) values were calculated by the MIC of Drug A (e.g., sulbactam/ampicillin) and Drug B (e.g., linezolid or arbekacin) in combination/MIC of Drug A or B alone. The FIC index was determined according to the following formula:

$$FIC\ index = \frac{MIC(\text{Drug } A \text{ in combination})}{MIC(\text{Drug } A \text{ alone})} + \frac{MIC(\text{Drug } B \text{ in combination})}{MIC(\text{Drug } B \text{ alone})}$$

The FIC indices were interpreted as follows: synergism was defined as an FIC index $\leq 0.5$, antagonism as an FIC index $\geq 2$, additivity as an FIC index $>0.5$ to $\leq 1.0$, and indifference as an FIC index $>1$ to $\leq 2$. The MIC and the FIC index values for the 48 MRSA strains tested are reported below in Table 1.

TABLE 1

MIC and FIC Index Values for Active Agents Alone and in Combination

| | | MIC Values (mcg/mL) | | | | | | | | | FIC Index | |
|---|---|---|---|---|---|---|---|---|---|---|---|---|
| Ex. | Strains | VCM | TEIC | LZD | ABK | ABPC | S/A | CZX | IPM | MPIPC | nitrocefin | S/A + LZD | S/A + ABK |
| 1 | JSCC 340 | 1 | 1 | 2 | 1 | 64 | 16 | >128 | 64 | >128 | + | 0.5 | 0.75 |
| 2 | JSCC 351 | 1 | 1 | 2 | 1 | 32 | 16 | >128 | 32 | >128 | + | 0.5625 | 0.5625 |
| 3 | JSCC 363 | 1 | 1 | 2 | 1 | 16 | 16 | >128 | 32 | >128 | − | 0.5625 | 0.625 |
| 4 | JSCC 381 | 1 | 1 | 2 | 0.5 | 32 | 16 | >128 | 32 | >128 | + | 0.75 | 2 |
| 5 | JSCC 390 | 1 | 1 | 2 | 0.5 | 32 | 16 | >128 | 32 | >128 | + | 0.5 | 0.53125 |
| 6 | JSCC 401 | 1 | 2 | 2 | 0.5 | 128 | 32 | >128 | 64 | >128 | + | 0.75 | 2 |
| 7 | JSCC 413 | 1 | 2 | 2 | 1 | 16 | 16 | >128 | 16 | >128 | − | 0.5 | 0.625 |
| 8 | JSCC 431 | 0.5 | 0.5 | 2 | 1 | 64 | 32 | >128 | 1 | 128 | + | 0.75 | 2 |
| 9 | JSCC 440 | 1 | 2 | 2 | 0.25 | 32 | 16 | >128 | 16 | >128 | + | 0.5625 | 1 |
| 10 | JSCC 451 | 1 | 2 | 2 | 4 | 16 | 32 | >128 | 64 | >128 | + | 0.625 | 0.75 |
| 11 | JSCC 463 | 1 | 1 | 2 | 0.5 | 16 | 16 | >128 | 64 | >128 | + | 0.75 | 0.625 |
| 12 | JSCC 481 | 1 | 2 | 2 | 1 | 64 | 32 | >128 | 64 | >128 | + | 0.375 | 0.5625 |
| 13 | JSCC 490 | 1 | 2 | 2 | 0.5 | 64 | 16 | >128 | 32 | >128 | + | 0.53125 | 0.625 |
| 14 | JSCC 501 | 1 | 2 | 2 | 0.5 | 32 | 16 | >128 | 32 | >128 | + | 0.53125 | 0.75 |
| 15 | JSCC 513 | 1 | 1 | 1 | 0.25 | 16 | 16 | >128 | 8 | 128 | + | 0.75 | 1 |
| 16 | JSCC 531 | 1 | 1 | 1 | 0.5 | 32 | 16 | >128 | 32 | >128 | + | 0.75 | 0.625 |
| 17 | JSCC 540 | 1 | 1 | 1 | 1 | 32 | 16 | >128 | 64 | >128 | + | 1 | 0.53125 |
| 18 | JSCC 551 | 0.5 | 1 | 2 | 2 | 16 | 16 | >128 | 16 | 128 | + | 0.75 | 0.75 |
| 19 | JSCC 563 | 1 | 2 | 1 | 0.125 | 1 | 2 | 16 | $\leq 0.125$ | 2 | + | 0.75 | 1 |
| 20 | JSCC 581[1] | 1 | 8 | 2 | 0.5 | 0.5 | $\leq 0.5$ | 16 | $\leq 0.125$ | 1 | + | — | — |
| 21 | JSCC 590[1] | 1 | 8 | 2 | 0.25 | 0.5 | $\leq 0.5$ | 16 | $\leq 0.125$ | 1 | + | — | — |
| 22 | JSCC 601 | 0.5 | 1 | 1 | 0.25 | 16 | 1 | >128 | 1 | 64 | − | 2 | 2 |
| 23 | JSCC 640 | 1 | 1 | 1 | 2 | 16 | 16 | >128 | 32 | >128 | − | 1 | 0.625 |
| 24 | JSCC 651 | 1 | 2 | 2 | 1 | 64 | 16 | >128 | 32 | >128 | + | 0.53125 | 0.5 |
| 25 | JSCC 663 | 1 | 1 | 2 | 0.5 | 16 | 16 | >128 | 8 | 128 | + | 0.75 | 0.53125 |
| 26 | ATCC 29213[2] | 1 | 1 | 2 | 0.25 | 0.5 | $\leq 0.5$ | 8 | $\leq 0.125$ | 0.25 | — | — | — |
| 27 | JSCC 681 | 1 | 0.5 | 0.5 | 1 | 16 | 16 | >128 | 8 | >128 | + | 1 | 0.5625 |
| 28 | JSCC 690 | 1 | 1 | 1 | 2 | 16 | 16 | >128 | 16 | 128 | + | 0.75 | 0.5 |
| 29 | JSCC 701 | 1 | 1 | 1 | 1 | 32 | 16 | >128 | 32 | >128 | + | 0.53125 | 0.53125 |
| 30 | JSCC 713 | 2 | 2 | 2 | 2 | 16 | 16 | >128 | 32 | >128 | + | 0.53125 | 0.53125 |
| 31 | JSCC 731 | 0.5 | 1 | 1 | 0.5 | 32 | 16 | >128 | 32 | >128 | + | 0.5 | 0.75 |
| 32 | JSCC 740 | 0.5 | 1 | 2 | 0.125 | 16 | 8 | >128 | 16 | 128 | + | 0.5 | 1 |
| 33 | JSCC 751 | 0.5 | 1 | 2 | 2 | 64 | 16 | >128 | 32 | >128 | + | 0.53125 | 0.5625 |
| 34 | JSCC 763 | 0.5 | 1 | 2 | 0.25 | 8 | 8 | >128 | 8 | 128 | − | 0.56235 | 0.5 |
| 35 | JSCC 781 | 2 | 4 | 2 | 2 | 16 | 16 | >128 | 32 | >128 | − | 0.75 | 1 |
| 36 | JSCC 870 | 1 | 1 | 2 | 0.5 | 32 | 16 | >128 | 16 | 128 | + | 0.53125 | 1 |
| 37 | ATCC29213[2] | 0.5 | 1 | 2 | 0.25 | 0.25 | <0.50 | 4 | $\leq 0.125$ | 0.25 | — | — | — |
| 38 | Mu 3 | 1 | 8 | 2 | 2 | 32 | 32 | >128 | 128 | >128 | — | 0.5 | 1 |
| 39 | Mu 50 | 4 | 16 | 2 | 4 | 32 | 16 | >128 | 64 | >128 | — | 0.5 | 0.5 |
| 40 | HIP 5827 | 4 | 16 | 2 | 1 | 64 | 16 | >128 | 64 | >128 | — | 0.75 | 0.625 |
| 41 | HIP 5836 | 4 | 8 | 2 | 1 | 16 | 2 | >128 | 8 | 128 | — | 0.625 | 0.5 |
| 42 | HIP 6297 | 2 | 4 | 2 | 0.125 | 16 | 8 | >128 | 1 | 64 | — | 0.5 | 0.625 |

TABLE 1-continued

MIC and FIC Index Values for Active Agents Alone and in Combination

| | | MIC Values (mcg/mL) | | | | | | | | | | FIC Index | |
|---|---|---|---|---|---|---|---|---|---|---|---|---|---|
| Ex. | Strains | VCM | TEIC | LZD | ABK | ABPC | S/A | CZX | IPM | MPIPC | nitrocefin | S/A + LZD | S/A + ABK |
| 43 | HIP 7737 | 4 | 16 | 2 | 0.125 | 32 | 8 | >128 | 32 | >128 | — | 0.5 | 0.5625 |
| 44 | AMC 11094 | 4 | 16 | 2 | 0.25 | 16 | 8 | >128 | 32 | >128 | — | 2 | 2 |
| 45 | 99.3759V | 2 | 16 | 2 | 2 | 64 | 16 | >128 | 64 | >128 | — | 0.625 | 1 |
| 46 | 99.3700W | 2 | 4 | 2 | 4 | 32 | 16 | >128 | 32 | >128 | — | 0.75 | 1 |
| 47 | BM12612(new) | 2 | 4 | 2 | 2 | 64 | 32 | >128 | 128 | >128 | — | 0.5 | 1 |
| 48 | LIM 2 | 2 | 8 | 1 | 1 | 32 | 4 | >128 | 8 | 128 | — | 0.5625 | 0.5625 |
| 49 | NCTC 10442 | 1 | 2 | 2 | 0.125 | <128 | 8 | >128 | 64 | >128 | — | 0.5 | 0.75 |
| 50 | 85/2082 | 1 | 1 | 2 | 0.25 | 32 | 8 | >128 | 2 | 64 | — | 0.5 | 0.5 |
| 51 | N315 | 0.5 | 0.5 | 2 | 0.5 | 8 | 8 | 64 | 1 | 16 | — | 1 | 0.625 |
| 52 | H1 | 0.5 | 4 | 2 | 1 | 16 | 32 | 2048 | 64 | 128 | — | 0.625 | 0.625 |

These strains lack the mecA gene. Indicates control sample.

In total, 48 MRSA strains were tested, including ten VRSA strains isolated from five different countries in the world, 33 MRSA strains isolated from ten Japanese university hospitals, and five MRSA type strains from Juntendo University, Department of Bacteriology, Tokyo, Japan. $MIC_{50}$s of linezolid and sulbactam/ampicillin were 2 and 32, respectively. A summary of the in vitro susceptibility of the 48 strains is shown below in Table 2.

TABLE 2

In vitro Susceptibility of 48 MRSA strains.

| Antimicrobial Agent | MRSA strains (n = 38) MICs (mg/L) | | | VRSA strains (n = 10) MICs (mg/L) | | |
|---|---|---|---|---|---|---|
| | Range | 50% | 90% | Range | 50% | 90% |
| Ampicillin | 1–>128 | 16 | 64 | 16–64 | 32 | 64 |
| Ampicillin sulbactam | 2–32 | 16 | 32 | 2–32 | — | — |
| Arbekacin | 0.125–4 | 0.5 | 2 | 0.125–4 | 1 | 4 |
| Ceftizoxime | 16–>128 | >128 | >128 | >128 | >128 | >128 |
| Imipenem | >0.125–128 | 16 | 64 | 1–128 | 32 | 64 |
| Linezolid | 0.5–2 | 2 | 2 | 1–2 | 2 | 2 |
| Oxacillin | 2–>128 | >128 | >128 | 64–>128 | >128 | >128 |
| Teicoplanin | 0.5–4 | 1 | 2 | 4–16 | | |
| Vancomycin | 0.5–2 | — | — | 2–4 | — | — |

Against ten VRSA strains, the combination exhibited synergism for four strains and additivity for five strains.

Against 38 MRSA strains, the combination exhibited synergism for nine strains and additivity for 28 strains. The FIC indices of the combinations are shown below in Table 3.

TABLE 3

FIC Indices of Ampicillin/Sulbactam in Combination with Linezolid or Arbekacin

| | Ampicillin/ Sulbactam | | Combination Effect | | | |
|---|---|---|---|---|---|---|
| Organism (n)[3] | Combined with: | FIC Index | Synergy | Additive | Indifference | Antagonism |
| MRSA[4] (38) | Linezolid | 0.375–2 | 9/38 | 28/38 | 1/38 | 0/38 |
| | Arbekacin | 0.5–2 | 3/38 | 30/38 | 5/38 | 0/38 |
| VRSA (10) | Linezolid | 0.5–2 | 4/10 | 5/10 | 1/10 | 0/10 |
| | Arbekacin | 0.5–2 | 2/10 | 7/10 | 1/10 | 0/10 |

[3]Where "n" indicates the number of strains.
[4]Includes 2 pre-MRSA strains

As evidenced by the data, linezolid had a susceptible range of MICs for all tested MRSA isolates, including VRSA strains. The combination of linezolid with ampicillin/sulbactam exhibited either synergy or additive effect against 46 of 48 tested MRSA strains. No antagonism was observed.

In addition, time-kill curve studies were performed for two strains (hetero-VRSA Mu3 and VRSA Mu50). Tubes containing 4 mL of trypticase-soy broth (TSB) with or without various concentrations of antibiotics were inoculated with overnight culture cells (final inocula of $10^5$ CFU/mL approximately) and incubated at 37° C. with shaking. Samples were taken at 1, 1.5, 3, 6, and 24 h and diluted with 0.9% NaCl and plated on H1 agar and incubated for overnight for counting the number of viable cells.

Time-kill studies of linezolid and sulbactam/ampicillin alone and in combination against the two strains showed that the combination of linezolid and sulbactam/ampicillin significantly increased in bacterial killing at 24 h incubation. The combination of linezolid and ampicillin/sulbactam exhibited sub-MIC cytokilling effect against both strains.

Accordingly, linezolid in combination with sulbactam and ampicillin provides promising activity in the treatment of extremely resistant strains of microorganisms, for example vancomycin-refractory MRSA infection. The combination can be useful in the treatment of MRSA infection, including infections caused by MRSA strains with reduced susceptibility to glycopeptides.

The foregoing detailed description is given for clearness of understanding only, and no unnecessary limitations should be understood therefrom, as modifications within the scope of the invention may become apparent to those skilled in the art.

What is claimed is:

1. A composition having antibacterial activity comprising an antibacterial effective amount of an oxazolidinone compound, an antibacterial effective amount of ampicillin, and an antibacterial enhancing amount of sulbactam.

2. The composition of claim 1 wherein the oxazolidinone compound is a compound of the formula:

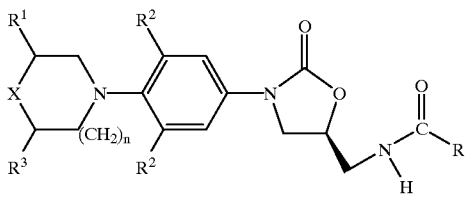

or a pharmaceutically acceptable salt thereof, wherein:
X is O, S, SO, $SO_2$, $SNR^{11}$, $NC(O)R^{11}$, or $S(O)NR^{11}$;
n is 0, 1, or 2;
R is selected from the group consisting of:
hydrogen;
$C_1$–$C_8$ alkyl optionally substituted with one or more substituents selected from the group consisting of F, Cl, hydroxy, $C_1$–$C_8$ alkoxy, $C_1$–$C_8$ acyloxy, and —$CH_2$— phenyl;
$C_3$–$C_6$ cycloalkyl;
amino;
$C_1$–$C_8$ alkylamino;
$C_1$–$C_8$ dialkylamino; and
$C_1$–$C_8$ alkoxy;
$R^1$ at each occurrence is hydrogen, except when X is O, then $R^1$ independently selected from the group consisting of H, $CH_3$, CN, $CO_2H$, $CO_2R$, and $(CH_2)_mR^{10}$, wherein m is 1 or 2;
$R^2$ at each occurrence is independently selected from the group consisting of H, F, and Cl;
$R^3$ is H, except when X is O and $R^1$ is $CH_3$, then $R^3$ is H or $CH_3$;
$R^{10}$ is selected from the group consisting of H, OH, OR, OCOR, $NH_2$, NHCOR, and $N(R^{11})_2$; and
$R^{11}$ at each occurrence is independently selected from the group consisting of H, p-toluensulfonyl, and $C_1$–$C_4$ alkyl optionally substituted with one or more substituents selected from the group consisting of Cl, F, OH, $C_1$–$C_8$ alkoxy, amino, $C_1$–$C_8$ alkylamino, and $C_1$–$C_8$ dialkylamino.

3. The composition of claim 1 wherein the oxazolidinone compound is selected from the group consisting of:
(S)-N-[[3-[3-fluoro-4-(4-morpholinyl)phenyl]-2-oxo-5-oxazolidinyl]methyl]acetamide (linezolid),
(S)-N-[[3-[3-fluoro-4-[4-(hydroxyacetyl)-1-piperazinyl]-phenyl]-2-oxo-5-oxazolidinyl]methyl]acetamide (eperezolid),
(S)-N-[[3-[3-fluoro-4-(tetrahydro-2H-thiopyran-4-yl)phenyl]-2-oxo-5-oxazolidinyl]methyl]acetamide S,S-dioxide, and
(S)-N-[[3-[3,5-difluoro-4-(tetrahydro-2H-thiopyran-4-yl)phenyl]-2-oxo-5-oxazolidinyl]methyl]acetamide S,S-dioxide.

4. The composition of claim 1 wherein the oxazolidinone compound is linezolid.

5. The composition of claim 1 wherein the pharmaceutically acceptable carrier comprises one or more inert excipients selected from the group consisting of mannitol, maize starch, colloidal silica, povidone, and magnesium stearate.

6. The composition of claim 1 wherein the composition is surrounded by a receptacle comprising at least 50 wt. % polyolefin.

7. A composition having antibacterial activity effective against a resistant strain of bacteria selected from the group consisting of methicillin-resistant Staphylococcus aureus (MRSA), vancomycin-resistant Enterococci (VRE), glycopeptide-intermediate Staphylococcus aureus (GISA), and vancomycin-intermediate Staphylococcus aureus (VISA), the composition comprising an antibacterial effective amount of an oxazolidinone compound, an antibacterial effective amount of ampicillin, and an antibacterial enhancing amount of sulbactam.

8. A method for treating a bacterial infection in a patient comprising the step of administering to a patient in need of such treatment an antibacterial effective amount of an oxazolidinone compound, an antibacterial effective amount of ampicillin, and an antibacterial enhancing amount of sulbactam.

9. The method of claim 8 wherein any two of said oxazolidinone compound, said sulbactam, and said ampicillin are administered in a single pharmaceutical composition.

10. The method of claim 8 wherein all of said oxazolidinone compound, said sulbactam, and said ampicillin are administered in a single pharmaceutical composition.

11. The method of claim 8 wherein the patient is a warm-blooded mammal.

12. The method of claim 8 where the patient is selected from the group consisting of a human, a horse, a cow, a dog, a cat, a sheep, and a pig.

13. The method of claim 8 wherein the patient is a human.

14. The method of claim 8 further comprising the steps of:
a) admixing said oxazolidinone compound, said sulbactam, and said ampicillin to provide a therapeutically effective mixture;
b) incorporating the mixture into a pharmaceutically acceptable carrier to form a composition; and
c) administering the composition to a patient in need of such treatment.

15. The method of claim 8 wherein the oxazolidinone compound is a compound of the formula:

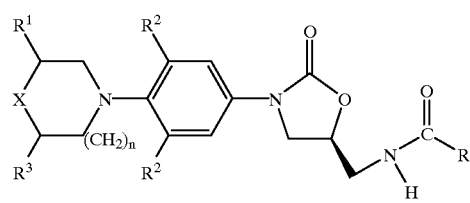

or a pharmaceutically acceptable salt thereof, wherein:
X is O, S, SO, $SO_2$, $SNR^{11}$, $NC(O)R^{11}$, or $S(O)NR^{11}$;
n is 0, 1, or 2;
R is selected from the group consisting of:
hydrogen;
$C_3$–$C_8$ alkyl optionally substituted with one or more substituents selected from the group consisting of F, Cl, hydroxy, $C_1$–$C_8$ alkoxy, $C_1$–$C_8$ acyloxy, and —$CH_2$— phenyl;
$C_3$–$C_6$ cycloalkyl;
amino;
$C_1$–$C_8$ alkylamino;
$C_1$–$C_8$ dialkylamino; and
$C_1$–$C_8$ alkoxy;

$R^1$ at each occurrence is hydrogen, except when X is O, then $R^1$ is independently selected from the group consisting of H, $CH_3$, CN, $CO_2H$, $CO_2R$, and $(CH_2)_m R^{10}$, wherein m is 1 or 2;

$R^2$ at each occurrence is independently selected from the group consisting of H, F, and Cl;

$R^3$ is H, except when X is O and $R^1$ is $CH_3$, then $R^3$ is H or $CH_3$;

$R^{10}$ is selected from the group consisting of H, OH, OR, OCOR, $NH_2$, NHCOR, and $N(R^{11})_2$; and $R^{11}$ at each occurrence is independently selected from the group consisting of H, p-toluensulfonyl, and $C_1$–$C_4$ alkyl optionally substituted with one or more substituents selected from the group consisting of Cl, F, OH, $C_1$–$C_8$ alkoxy, amino, $C_1$–$C_8$ alkylamino, and $C_1$–$C_8$ dialkylamino.

16. The method of claim 8 wherein the oxazolidinone compound is selected from the group consisting of:
(S)-N-[[3-[3-fluoro-4-(4-morpholinyl)phenyl]-2-oxo-5-oxazolidinyl]methyl]acetamide (linezolid),
(S)-N-[[3-[3-fluoro-4-[4-(hydroxyacetyl)-1-piperazinyl]-phenyl]-2-oxo-5-oxazolidinyl]methyl]acetamide (eperezolid),
(S)-N-[[3-[3-fluoro-4-(tetrahydro-2H-thiopyran-4-yl)phenyl]-2-oxo-5-oxazolidinyl]methyl]acetamide S,S-dioxide, and
(S)-N-[[3-[3,5-difluoro-4-(tetrahydro-2H-thiopyran-4-yl)phenyl]-2-oxo-S-oxazolidinyl]methyl]acetamide S,S-dioxide.

17. The method of claim 8 wherein the oxazolidinone compound is linezolid.

18. The method of claim 17 wherein the amount of linezolid administered is from about 200 mg to about 900 mg over a period of about 12 hours.

19. The method of claim 8 wherein the combined total amount of ampicillin and sulbactam administered is from about 3.1 grams to about 6.2 grams administered about every four hours to eight hours.

20. The method of claim 8 wherein said treatment is carried out for seven days to 60 days.

21. The method of claim 8 wherein the oxazolidinone compound, sulbactam and ampicillin are administered orally or intravenously.

22. The method of claim 8 wherein the treatment is administered two or three times daily.

23. The method of claim 8 wherein the antibacterial activity is effective against a resistant strain of bacteria selected from the group consisting of methicillin-resistant Staphylococcus aureus (MRSA), vancomycin-resistant Enterococci (VRE), glycopeptide-intermediate Staphylococcus aureus (GISA), and vancomycin-intermediate Staphylococcus aureus.

24. The method of claim 8 wherein the bacterial infection is a condition selected from the group consisting of endocarditis, osteomyelitis, meningitis, skin and skin structure infections, pneumonias, bacteremias, intra-abdominal infections, genitourinary tract infections, abscesses, and necrotizing infections.

25. The method of claim 8 wherein the patient has a condition of neutropenia.

26. The method of claim 8 wherein the patient has a condition of leukemia or lymphoma.

27. A medicament for preventing or treating a bacterial infection comprising an antibacterial effective amount of an oxazolidinone compound, an antibacterial effective amount of ampicillin, and an antibacterial enhancing amount of sulbactam.

28. The medicament of claim 27 wherein the oxazolidinone compound is a compound of the formula:

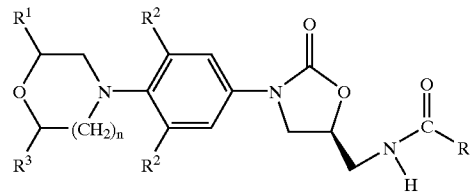

or a pharmaceutically acceptable salt thereof, wherein:
n is 0, 1, or 2;
R is selected from the group consisting of:
hydrogen;
$C_1$–$C_8$ alkyl optionally substituted with one or more substituents selected from the group consisting of Cl, hydroxy, $C_1$–$C_8$ alkoxy, $C_1$–$C_8$ acyloxy, and —$CH_2$— phenyl;
$C_3$–$C_6$ cycloalkyl;
amino;
$C_1$–$C_8$ alkylamino;
$C_1$–$C_8$ dialkylamino; and
$C_1$–$C_8$ alkoxy;

$R^1$ at each occurrence is independently selected from the group consisting of H, $CH_3$, CN, $CO_2H$, $CO_2R$, and $(CH_2)_m R^{10}$, wherein m is 1 or 2;

$R^2$ at each occurrence is independently selected from the group consisting of H, F, and Cl;

$R^3$ is H, except when $R^1$ is $CH_3$, then $R^3$ is H or $CD_3$;

$R^{10}$ is selected from the group consisting of H, OH, OR, OCOR, $NH_2$, NHCOR, and $N(R^{11})_2$; and $R^{11}$ at each occurrence is independently selected from the group consisting of H, p-toluensulfonyl, and $C_1$–$C_4$ alkyl optionally substituted with one or more substituents selected from the group consisting of Cl, F, OH, $C_1$–$C_8$ alkoxy, amino, $C_1$–$C_8$ alkylamino, and $C_1$–$C_9$ dialkylamino.

29. A composition having antibacterial activity effective against a resistant strain of bacteria selected from the group consisting of methicillin-resistant Staphylococcus aureus (MRSA), vancomycin-resistant Staphylococcus aureus (VRSA), glycopeptide-intermediate Staphylococcus aureus (GISA), and vancomycin-intermediate Staphylococcus aureus (VISA), the composition comprising an antibacterial effective amount of an oxazolidinone compound, an antibacterial effective amount of ampicillin, and an antibacterial enhancing amount of sulbactam.

30. The composition of claim 29 wherein the antibacterial activity is effective against a resistant strain of bacteria selected from the group consisting of methicillin-resistant Staphylococcus aureus (MRSA) and vancomycin-resistant Staphylococcus aureus (VRSA).

* * * * *